United States Patent [19]

Seder et al.

[11] Patent Number: 5,116,310
[45] Date of Patent: May 26, 1992

[54] MULTIPLE LUMEN WOUND DRAIN WITH BYPASS OPENINGS

[75] Inventors: Edmund V. Seder; Frederick L. Coe, both of Santa Barbara; Martin Mitchell, Oxnard, all of Calif.

[73] Assignee: Helix Medical, Inc., Santa Barbara, Calif.

[21] Appl. No.: 559,670

[22] Filed: Jul. 30, 1990

[51] Int. Cl.⁵ .................. A61M 3/00; A61M 25/00
[52] U.S. Cl. ......................... 604/43; 604/266; 604/282
[58] Field of Search ............ 604/27, 35, 43, 45, 604/49, 129, 264, 266, 268, 280, 282

[56] References Cited

U.S. PATENT DOCUMENTS

| | | | |
|---|---|---|---|
| 2,268,321 | 12/1911 | Flynn | 604/282 |
| 2,286,462 | 6/1942 | Chaffin | 604/43 |
| 3,583,404 | 6/1971 | McWhorter | 604/266 |
| 3,590,820 | 7/1971 | Nehra et al. | 604/268 |
| 4,182,343 | 1/1980 | Inaba | 604/268 |
| 4,398,910 | 8/1983 | Blake et al. | |
| 4,445,897 | 5/1984 | Ekbladh et al. | 604/43 |
| 4,465,481 | 8/1984 | Blake | |
| 4,508,533 | 4/1985 | Abramson | 604/45 |
| 4,573,965 | 3/1985 | Russo | 604/45 |
| 4,650,463 | 3/1987 | LeVeen et al. | |
| 4,795,439 | 1/1989 | Guest | 604/280 |

FOREIGN PATENT DOCUMENTS 8500526 2/1985 World Int. Prop. O. .......... 604/266

Primary Examiner—John D. Yasko
Assistant Examiner—Anthony Gutowski
Attorney, Agent, or Firm—Marvin E. Jacobs

[57] ABSTRACT

A silicone catheter wound drain with parallel lumens or passageways formed inside to convey fluid from a wound. The drain has both holes and slots on the outside surface to admit fluid to the lumens and internal openings between the lumens to divert fluid from a blocked lumen to an adjacent lumen and back again after the blockage. The silicon wound drain may contain an embedded, elongated reinforcing fiber to strengthen the wound drain and prevent necking down during removal.

3 Claims, 1 Drawing Sheet

MULTIPLE LUMEN WOUND DRAIN WITH BYPASS OPENINGS

TECHNICAL FIELD

This invention relates to the medical arts, particularly to catheters that are positioned in wounds to drain fluid therefrom during healing of the wound. More specifically, a flexible wound drain is disclosed that is more resistant to internal blockage an obstruction.

BACKGROUND OF THE INVENTION

Prior art wound drains commonly comprise soft and flexible tubes, usually made of silicone, with openings in the tube wall. The openings may range in shape from small round holes to extended or even continuous slots. When the drain is placed in the wound, and the wound closed, fluids and other wound debris can flow through the openings to the interior of the tube and exit the wound through the tube. A vacuum source is often connected to the exit end of the tube to encourage drainage and maintain sterile conditions.

In anatomy, the passage within a tubular organ is called a lumen. This terminology has been adapted to describe the passageway inside the wound drain tube as well. Prior art wound drains have been made in the form of tubes with a single lumen or passageway, and also with multiple lumens to resist kinking and pinching. Multiple lumens hopefully reduce the chances that all of the drain paths will be blocked by wound debris, clots, or physical distortions of the drain. However, such solutions are less than satisfactory because for any given drain size, more lumens necessitate smaller diameter lumens. Accordingly, what is gained by redundancy is offset by a lumen size more susceptible to clogging and obstruction.

STATEMENT OF THE PRIOR ART

U.S. Pat. Nos. 4,398,910 and 4,465,481 to Blake et al discloses a silicone wound drain using multiple lumens in which the openings on the outside of the drain are continuous slots so as to insure a uniform cross-sectional area everywhere along the length of the drain. The theory of this design is to avoid any holes whatsoever in the drain because the holes would vary the cross-sectional area and thus create weak points. Blake teaches that these weak points encourage kinking when the drain is bent and breakage when the drain is extracted.

Blake further teaches that this uniform cross-section design, being made of soft silicone, necks down to a lesser diameter upon extraction, when it is pulled, thus facilitating easy removal. However, this softness exacerbates the blockage problem. The soft silicone can be more easily squeezed shut to block the lumens therein. The present invention significantly reduces the chances of blockage caused by unavoidable mechanical forces on the drain that result from necking down, pinching, or kinks.

SUMMARY OF THE INVENTION

The present invention advances wound drain design with a new topological arrangement that greatly reduces the likelihood of total drain blockage. Multiple lumens, three are described in the preferred embodiment, extend along the length of the drain to channel fluid out of the wound. In addition, a large plurality of transverse bypass passages are distributed along the length of the drain so as to interconnect the lumens at numerous locations. If a lumen becomes pinched or blocked somewhere, the fluid flow in that lumen can divert through a transverse bypass passage into another parallel lumen. Once past the blockage, the flow can again return to the original lumen by way of another bypass passage. In effect, the network of redundantly interconnected multiple lumens offers a multitude of different possible drain paths without having to use more and smaller lumens.

The only way the drain can be blocked is by the simultaneous obstruction of all of the lumens at exactly the same location, an improbable occurrence.

To further improve the present invention, optional longitudinal reinforcement fibers may be embedded in the drain to both strengthen the drain and avoid the necking down effect described in the Blake et al patent. If the drain were stretched during use, and did neck down, the lumens could be reduced in diameter at one location by this necking down effect. This would make more probable the obstruction of all the lumens at the same location.

The following detailed description shows two possible embodiments of the invention that provide multiple interconnected lumens in a configuration that is optimal for manufacture by both molding and extruding techniques. Additional advantages and improvements will also become apparent.

DETAILED DESCRIPTION OF THE INVENTION

Figure 1:
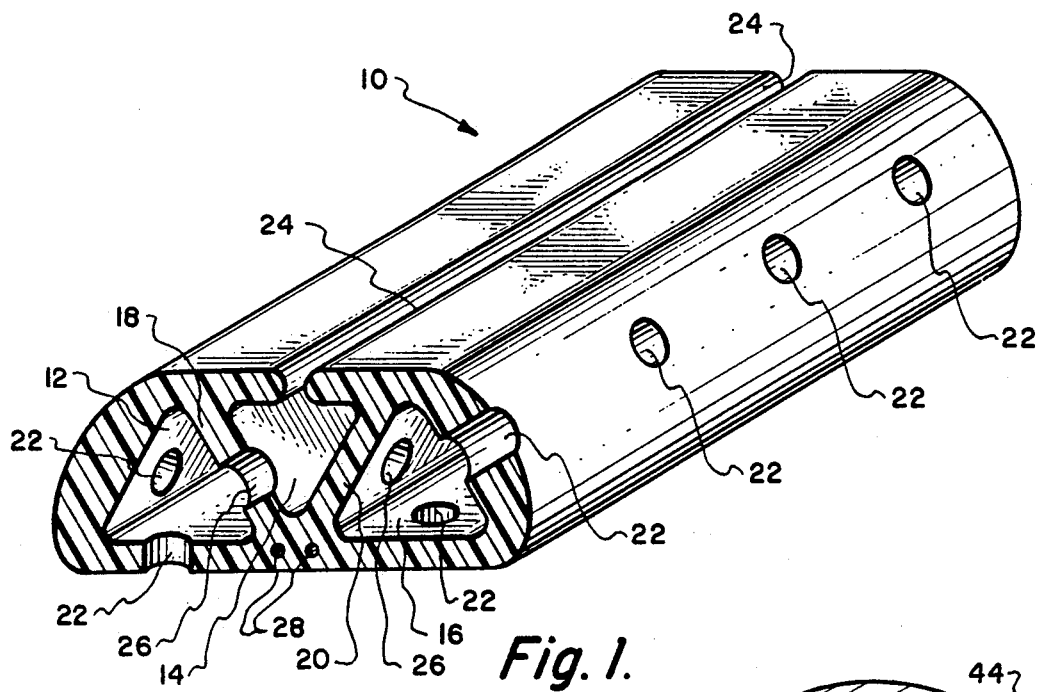
FIG. 1 is a perspective view of a short section of a wound drain constructed in accordance with the principles of the present invention and having a flattened profile which shape is preferred in some surgical situations.

A short section of the wound drain 10 is shown in perspective in FIG. 1. Three lumens or channels 12, 14, and 16 extend along and throughout the length of the drain 10. These lumens are separated from each other by walls 18 and 20. In the preferred embodiment, the lumens are generally triangular in cross section so that walls 18 and 20 cooperate with the outside walls to create a truss shaped internal structure that supports drain 10 against collapse in the event of externally applied pressure from surrounding tissue or fasteners.

Fluids from the wound enter drain 10 through suitable openings in the outside walls of drain 10. Two kinds of openings are shown in FIG. 1. The first kind are rounded holes 22 which are either molded or punched into drain 10. The second kind is a continuous slot 24 which can be formed by molding, extruding, or cutting.

Bypass passages are formed by molding or punching openings 26 in walls 18 and 20. In FIG. 1, openings 26 are shown as generally round holes positioned at staggered locations along walls 18 and 20. Staggering the bypass holes 26 avoids unnecessary weakening of the drain in one place. Ideally, no more than one hole is positioned at any one cross sectional location. However, to enhance clarity in FIGS. 1 and 2, two and three holes are drawn at the same locations so that a single cross sectional plane may be employed to reveal different holes. In practice, however, the holes should be staggered as much as possible.

Embedded into drain 10 are a pair of reinforcing fibers 28. Fibers 28 strengthen drain 10 during use and extraction. Since drain 10 is formed from a soft and pliant material, for example, 50 Durometer silicone, deformation is a ready possibility. The reinforcing fibers 28 prevent tearing of the drain and also resist linear extension of the drain which could neck down lumens 12, 14, and 16 at the same position and increase the risk of blockage.

Fibers 28 are not so strong that they strip loose from the soft silicone drain. Instead, they are strong enough to resist elongation while still being similar in elongation characteristics to the drain. This is achieved by constructing fibers 28 from a plurality of cooperating fibers that are wound, weaved, coiled, or braided together so as to mechanically interact to the degree necessary to provide the desired strength and elongation. Such cords also bond well to the drain. The fibers may be formed from either thermoplastic or thermoset synthetic materials or any other biocompatible material with a higher tensile strength such as a Kevlar (an aromatic polyimide) or carbon graphite fibers which are compatible with and bind to the surrounding silicone material of the wound drain.

It has been found that both holes 22 and slot 24 are satisfactory openings to admit fluid into lumens 12, 14, and 16. However, in the preferred embodiment, it is desirable to have at least one slot type opening to facilitate the manufacture of the drain. One method of construction is to extrude silicone in the cross-sectional shape shown in FIG. 1. Slot 24 provides good access to lumen 14 and this, in turn, provides access to walls 18 and 20 so that the bypass holes 26 may be punched.

Another method of construction is to mold the drain about mandrels shaped to form the lumens. The mandrel for lumen 14 may have projections thereon to form holes 26 and still be easily removed through slot 24. The exterior wall openings 22 may be molded by projections on the outer mold that forms the exterior surface of drain 10. After removal of the exterior mold and the projection covered lumen 14 mandrel, it is relatively easy to withdraw the projectionless mandrels that form lumens 12 and 16 from the end provided the drain is not overly long.

Figure 2:
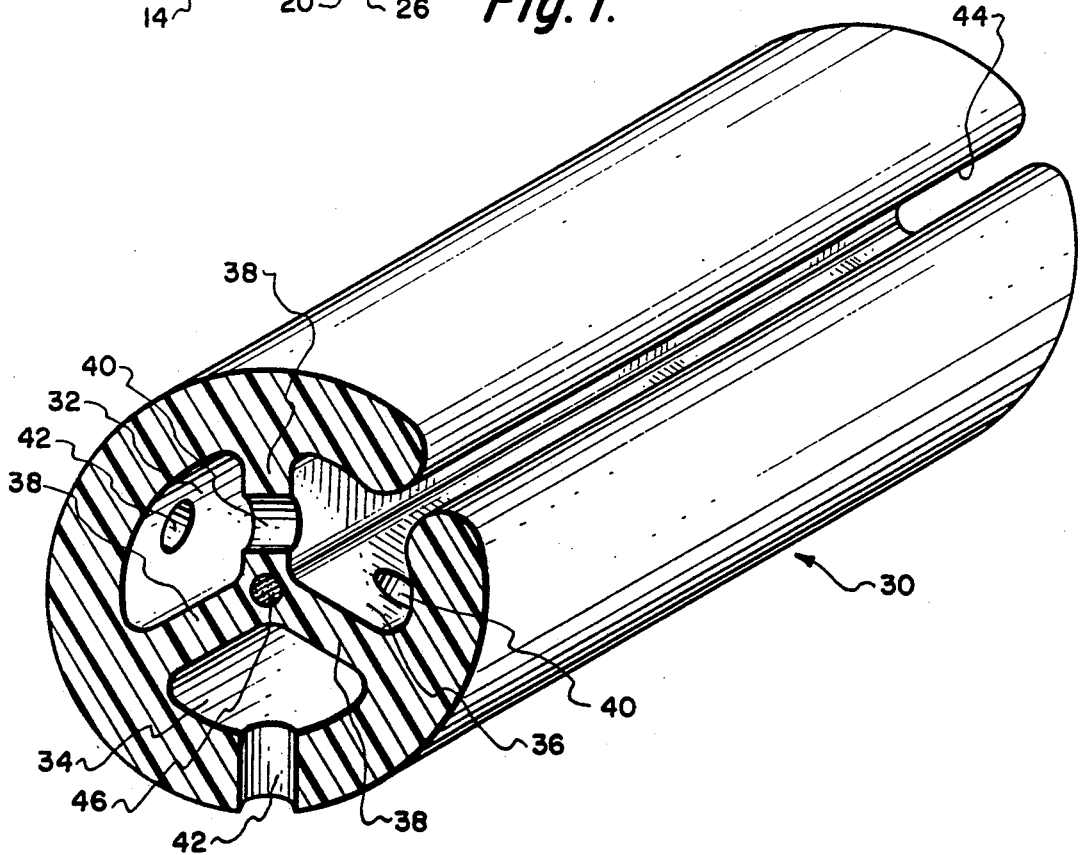
FIG. 2 shows another embodiment of the invention with a round profile and offering greater flow path redundancy due to the fact that each of the three lumens communicates with both of the other two lumens.

The features and principles discussed above also apply to the round profile drain 30 shown in FIG. 2. Drain 30 has three lumens 32, 34, and 36 separated by walls 38. Bypass holes 40 are formed at staggered locations in walls 38 while the outside openings comprise holes 42 or slots 44. A single reinforcing fiber 46 strengthens drain 30. The slightly different geometry of FIG. 2 puts each lumen in transverse communication with both of the other two lumens thus assuring maximum flexibility of the drain paths in the event one of the lumens is blocked. Of course, the number of lumens, their relative size and position, and the shape of the dividing walls are not essential to the spirit and scope of the invention a defined in the following claims.

We claim:

1. A wound drain comprising an elongate structure formed from a pliable and soft material with multiple parallel lumens in said structure, with external openings to the outside of the structure from said lumens and with bypass interconnecting openings between said luments, fluid flow from said wound being channeled through said external openings to said lumens so as to exit the wound and also channeled through said bypass openings to adjacent lumens when one or more of the lumens is obstructed, and in which said lumens are generally triangular in shape so that said drain has a truss shaped cross section to maximize resistance to mechanical compression.

2. A wound drain comprising an elongate structure formed from a pliable and soft silicone material with multiple parallel drain lumens in said structure, said drain lumens having approximately equal cross-sectional drain area, with external openings to the outside of the structure from said lumens and with bypass interconnecting openings between said lumens, fluid flow from said wound being channeled through said external openings to said lumens so as to exit the wound and also channeled through said bypass openings to adjacent lumens when one or more of the lumens is obstructed, in which one of said external openings comprises a slot formed continuously along the elongate structure in communication with one of said drain lumens while the remaining external openings are relatively small holes so that the other lumens comprise substantially tubular drain channels.

3. A wound drain comprising an elongate structure formed from a pliable and soft silicone material with multiple parallel lumens in said structure, with external openings to the outside of the structure from said lumens wand with bypass interconnecting openings between said lumens, fluid flow from said wound being channeled through said external openings to said lumens so as to exit the wound and also channeled through said bypass openings to adjacent lumens when one or more of the lumens is obstructed, in which at least one of said external openings comprises a slot formed continuously along the elongate structure in communication with a lumen, and including reinforcing means in said drain positioned parallel to the lumens so as to resist elongation of the drain and strengthen the drain, said reinforcing means comprising a plurality of cooperating fibers, and in which said lumens are approximately triangular so as to make the drain have a truss shaped cross section to resist collapse.

* * * * *